(12) United States Patent
Lawrence et al.

(10) Patent No.: US 6,944,882 B2
(45) Date of Patent: Sep. 20, 2005

(54) EYEGLASSES VISOR AND CASE

(76) Inventors: Richard Lawrence, 104 Fifth St. East, Tierra Verde, FL (US) 33715; Isabel Clare Lawrence, 104 Fifth St. East, Tierra Verde, FL (US) 33715

(*) Notice: Subject to any disclaimer, the term of this patent is extended or adjusted under 35 U.S.C. 154(b) by 0 days.

(21) Appl. No.: 10/852,061

(22) Filed: May 24, 2004

(65) Prior Publication Data

US 2005/0138715 A1 Jun. 30, 2005

Related U.S. Application Data

(60) Provisional application No. 60/533,677, filed on Dec. 30, 2003.

(51) Int. Cl.$^7$ ............................................... A61F 9/00
(52) U.S. Cl. ............................................... 2/13; 206/5
(58) Field of Search ........................... 2/10, 12, 13, 15, 2/209.13; 206/5, 6; 351/155

(56) References Cited

U.S. PATENT DOCUMENTS

| | | | | |
|---|---|---|---|---|
| 2,262,142 A | * | 11/1941 | Karmsen | 2/10 |
| 2,723,745 A | * | 11/1955 | McNeill | 206/5 |
| 4,543,667 A | * | 10/1985 | Garbutt | 2/13 |
| 4,606,453 A | * | 8/1986 | Burns | 206/5 |
| 5,032,019 A | * | 7/1991 | Burchett | 351/158 |
| 5,366,072 A | * | 11/1994 | Goldenberg | 206/5 |
| 5,913,416 A | * | 6/1999 | Rothan | 206/5 |
| 6,247,177 B1 | * | 6/2001 | Hayes | 2/12 |

\* cited by examiner

*Primary Examiner*—Katherine M. Moran
(74) *Attorney, Agent, or Firm*—Dennis L. Cook, Esq.

(57) ABSTRACT

This invention relates to a eyeglass case and visor with a novel method of attachment to the limbs of a pair of eyeglasses, so that the eyeglasses are firmly connected to the visor at the forehead of the wearer of the eyeglasses, in an attitude which keeps it from drooping into the vision range of the user. More particularly, the visor is formed of two plies of material, the top ply is crescent shaped and the bottom ply is crescent shaped with the corners removed to allow for a wide opening pocket and proper placement of attachment bands on the bottom of the top ply of material. The top and bottom plies of material are connected together along the convex edges of the top and bottom plies of material, but are left substantially unconnected along the other edges except for a fastening means, thereby forming a wide opening pocket in which the eyeglasses can be placed without removal of the eyeglass limbs from the visor attachment bands.

10 Claims, 5 Drawing Sheets

EYEGLASSES VISOR AND CASE

CROSS-REFERENCE TO RELATED APPLICATION

The present application claims the benefit of previously filed Provisional Patent Application Ser. No. 60/533,677 filed on Dec. 30, 2003.

FIELD OF THE INVENTION

This invention relates to the field of eyeglass visors and more particularly to an eyeglass visor and eyeglass case combination device that holds the visor firmly in place and allows the eyeglasses to be stored within the visor without detaching the visor from the eyeglass frame. The unique attachment points and their specific configuration also allow the widest variety of eyeglass frames to utilize the visor and case combination as opposed to prior art devices.

BACKGROUND OF THE INVENTION

This invention relates to a visor with a novel method of attachment to the limbs of a pair of eyeglasses, so that the eyeglasses are firmly connected to the visor and the connected visor is worn at the forehead of the wearer of the eyeglasses, in an attitude which allows it to shield the eyes from overhead sun yet still keeps it from significantly drooping down into the vision range of the user. In addition, the attachment bands are uniquely configured to hold a wide variety of eyeglass limbs of vastly different sizes snug to the visor as opposed to the relatively limited types of limbs addressed by the prior arts. More particularly, the visor is formed of two plies of material, the top ply is crescent shaped. The bottom ply is crescent shaped to match and attach to the convex edge of the top ply with the corners removed to allow for a wide opening pocket and proper placement of attachment bands on the bottom of the top ply of material. The opposing edge of the bottom ply is triangular shaped ending in a semicircular tab to extend beyond the concave edge of the top ply and fold over and attach to the top of the top ply. The top and bottom plies of material are connected together along the convex edges of the top and bottom plies of material but are left substantially unconnected along the other edges except for a fastening means, thereby forming a wide opening pocket in which the eyeglasses can be placed without removal of the eyeglass limbs from the visor attachment bands, thus allowing insertion of the eyeglasses into the pocket without removing them from the attachment points. The eyeglasses stay safely and firmly attached to the visor during visor use or case use applications allowing the user additional confidence that the eyeglass will remain secure for instance during vigorous activities, in windy conditions, etc.

Various visors or brims have been manufactured in the past for mounting at the forehead of a person so as to shade the eyes from the sun, etc. Most of the visors are attached to a hat which supports the visor at the forehead of the wearer of the hat. Also, some visors have been developed which comprise the visor with a band or clamp that extends rearwardly from the visor which is to fit about the head of the wearer so as to support the visor at the forehead of the wearer.

U.S. Pat. No. 4,606,453 issued to Burns discloses a visor comprising two plies of crescent shaped material are placed in overlying relationship, with the plies being attached along their convex edges. The concave edges remain unattached to each other, so that a pocket is formed between the plies of material. Loops are formed at opposite edges of the convex edge of the plies of material. The limbs of eyeglasses can inserted through the loops so that the plies of material form a visor at the forehead of the wearer of the eyeglasses. In the alternative, the eyeglasses can be removed from the visor and inserted into the pocket, so that the plies of material form a case for the eyeglasses. But, to utilize the case, the eyeglasses must be removed from the visor. Also, very large or very small limbs are not supported well with this system, causing poor fit to the visor and potential for the visor to compromise the vision of the wearer. Other patents disclosing similar visors that attach to eyeglasses include U.S. Pat. No. 5,533,321, U.S. Pat. No. 5,524,291, and U.S. Pat. No. 4,543,667.

None of these prior art patents disclose the unique features of this invention which allow for the eyeglasses and the visor to remain attached in visor use and also to be inserted in the visor/case while still being attached to the visor, or have the unique connection method to the eyeglass frame that keeps the visor firmly connected at the user's forehead and at an attitude that keeps it from drooping into the vision range of the user. The unique connection method also can accommodate the largest variety of different sized eyeglass limbs, thus establishing a strong advantage over prior art visors.

BRIEF DESCRIPTION OF THE INVENTION

Briefly described, the present invention comprises a sun visor that is to be worn at the forehead of a person, and which is removably attachable to the limbs of eyeglasses of the wearer, with the visor being attached to and supported by the eyeglasses, without a hat or band structure engaging the head of the wearer. The visor comprises a crescent shaped bill that has four elastic bands—one looped and one flat in a unique configuration at each of its two opposite corners, such that the limbs of the eyeglasses are inserted through the bands for connection to the visor and for firm support to the visor. For most eyeglass limb attachments, the looped and flat bands work together to support and stabilize the visor to the eyeglasses better than prior arts attachments and hold it in a position at the forehead of the user, causing the visor to be perched at a height slightly above the lenses of the eyeglasses and out of the range of vision of the user. The combination of flat and looped bands uniquely adapt to a large variety of limb sizes by offering attachment options to optimally suit a given set of limbs. For instance the thinnest limbs utilize both elastic bands to firmly support a visor, while a thick limb may utilize one or both looped elastic bands for the same degree of firm support. The visor may also be used without attachment to any glasses if preferred by the user by using a lanyard and cord stop to secure it firmly to the user's forehead.

The visor is formed from two plies of material. The top ply is formed of a semi rigid material in a crescent shape, having one concave edge and one convex edge, and the bottom ply is formed of a flexible material having a similar convex edge but with the corners removed. The opposing edge of the bottom ply is triangular shaped ending in a semicircular tab to extend beyond the concave edge of the top ply and fold over and attach to the top of the top ply. The plies of material are arranged in overlying relationship with the convex edges aligned. The plies of material are attached to each other along the convex edges, which leaves the other edges unattached except for a fastener means. This forms the top and bottom plies of material into a wide opening pocket having the unattached edges of the plies of material forming the pocket opening. The pocket is sized and shaped so as to receive the eyeglasses of the wearer or other similar sized objects. A unique set of attachment means to secure the eyeglasses to the visor are placed on the underside of the top ply in the general area where the corners are removed from the bottom ply such that the visor can remain attached to the eyeglass frame while either the eyeglasses are folded and placed in the visor pocket opening or unfolded and worn normally by the user, thus firmly securing the visor to the eyeglasses both during visor and storage applications.

Thus, it is an object of this invention to provide a visor that is removably mounted to eyeglasses, so that the visor can be snuggly supported to the eyeglass frame and positioned at the forehead of the wearer of the eyeglasses without additional support. The unique attachment bands allow this snug fit over the full range of eyeglass limbs from very thin and wire-like to very thick.

Another object of this invention is to provide a visor that functions both as an eyeglass visor at the face of the wearer of the visor and as a pocket for storing various objects such as eyeglasses and wherein the fold-over of the closure flap allows for the closure of the pocket and the folded-over material forms a soft barrier at the forehead which cushions the forehead from the edges of the pocket.

Another object of this invention is to provide a visor that functions both as an eyeglass visor at the face of the wearer of the visor and as a pocket for storing various objects such as eyeglasses wherein the eyeglasses or other objects can be placed within the pocket without removal of the eyeglasses from the visor.

Other objects, features and advantages of the present invention will become apparent upon reading the following specification, when taken in conjunction with the accompanying drawings.

BRIEF DESCRIPTION OF THE DRAWINGS

For a fuller understanding of the nature and objects of the invention, reference should be made to the following detailed description, taken in connection with the accompanying drawings, in which.

DETAILED DESCRIPTION

Figure 1:
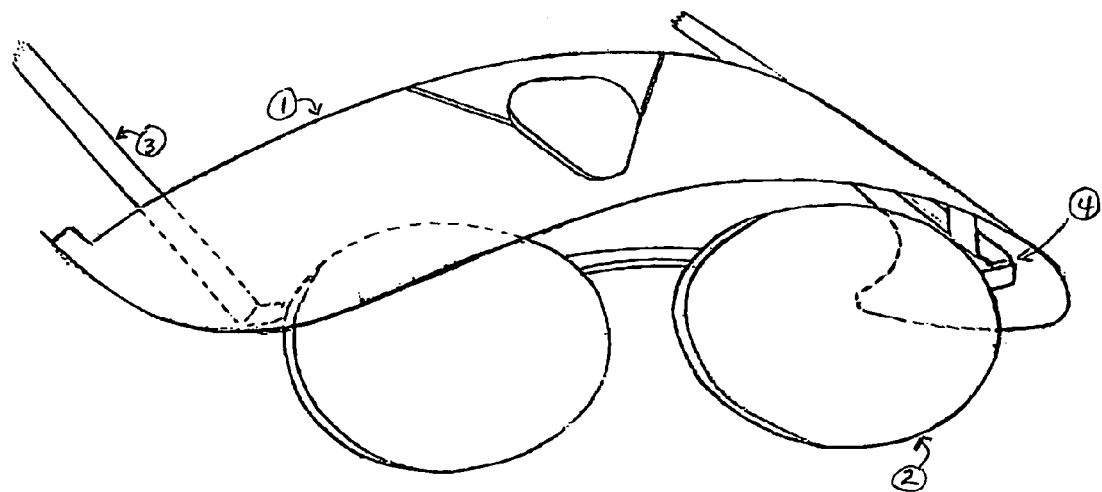
FIG. 1 is a perspective illustration of the eyeglasses visor and case, showing the visor and case attached to a pair of eyeglasses.

Referring now in more detail to the drawings, in which like numerals indicate like parts throughout the several views, FIG. 1 illustrates the eyeglasses visor and case (1) mounted to a pair of eyeglasses (2). The eyeglasses (2) are of conventional design and include lenses and frame, such frame including foldable limbs (3) and (4).

Figure 2:
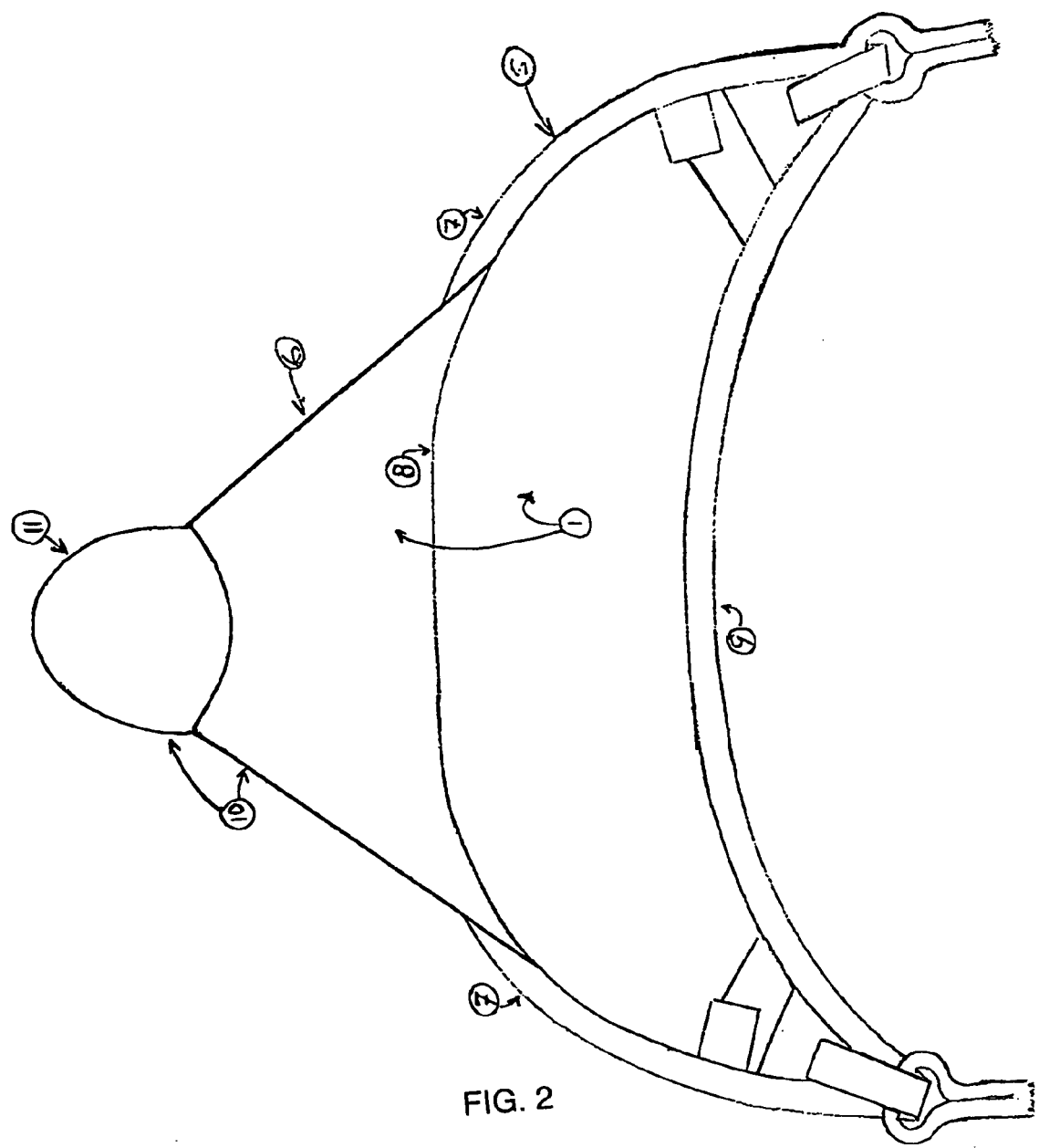
FIG. 2 is a view of the visor and case showing the top and bottom plies.

As shown in FIG. 2 the visor and case (1) is formed from a top ply of rigid crescent shaped material (5) that includes a convex edge (7), and a concave edge (9). The bottom ply (6) is formed of a flexible material having a similar convex edge (8) but with the corners removed. The opposing edge (10) of the bottom ply (6) is triangular shaped ending in a semicircular tab to extend beyond the concave edge (9) of the top ply (5) and fold over and attach to the top of the top ply (5). The convex edges (7,8) are attached together along their lengths, as by stitching or adding a banding trim in the usual manner well known to those skilled in the art. Therefore, the visor case is open at the opposing edges (9,10), so that the plies of material form a pocket and the bottom ply (6) triangular shaped edge (10) can be folded over and attach to the top of the top ply (5) thus closing the pocket and forming a cushion of soft material against the forehead of the user. In the preferred embodiment the visor and case (1) is constructed of a fashion fabric top attached to a rigid material such as foam which create the top ply of crescent shaped material (5). The bottom ply (6) is constructed of soft stretchy material. These materials are well known to those skilled in the art. Surfaces which come in contact with the eyeglasses are chosen to be soft material so as not to scratch the eyeglasses.

A releasable fastener means (11) is used to close the pocket. The fastener means (1) illustrated herein are an overlying flap attached to the bottom ply (6) and foldable over and attachable to the top ply (5) by loop and hook connection elements known by the tradename Velcro. Obviously, other fasteners such as snaps, buttons, zippers, etc., could be used if desired.

Figure 3:
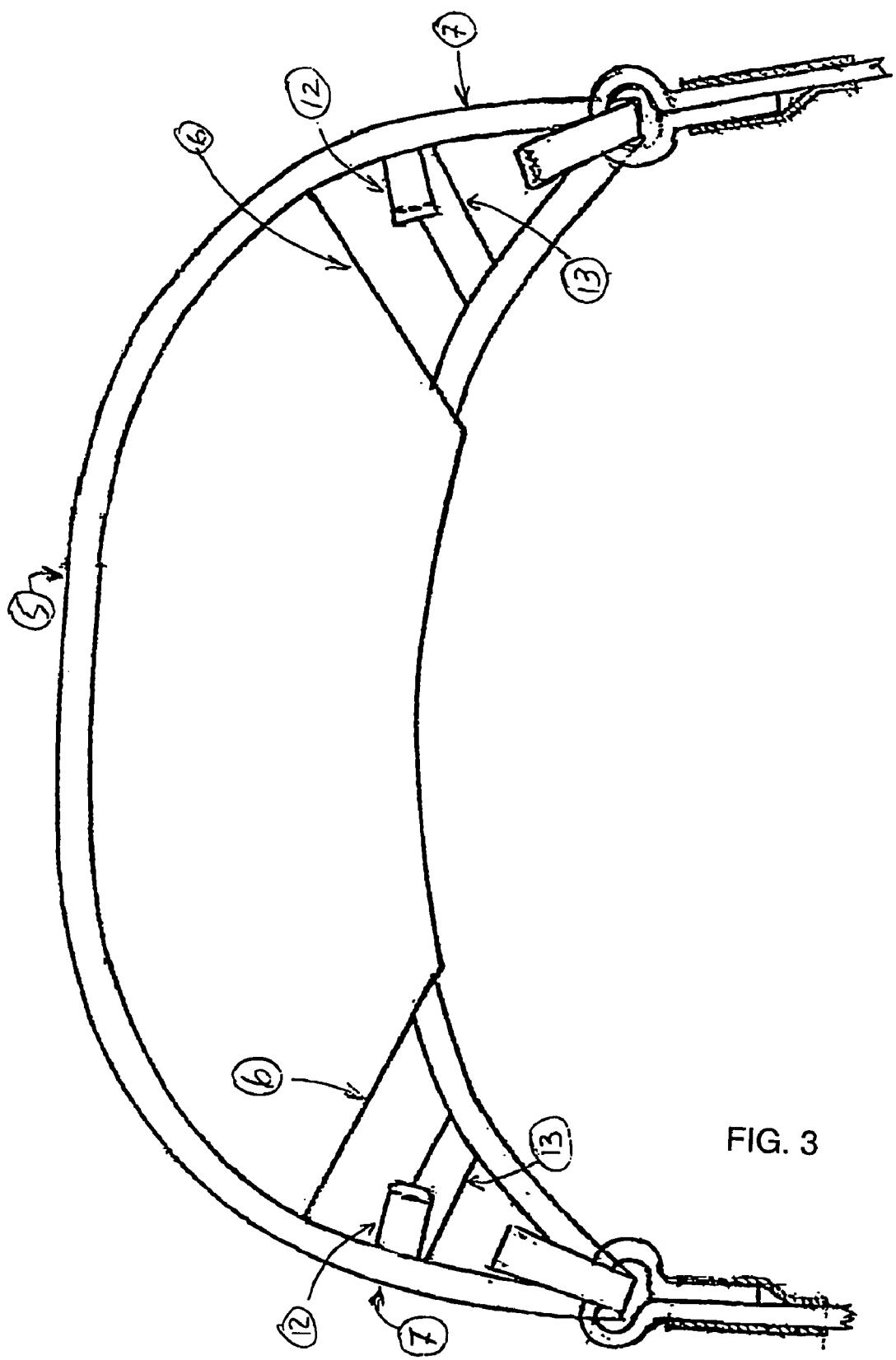
FIG. 3 is a bottom view of the visor and case showing the attachment bands on the exposed bottom of the top ply.
Figure 4:
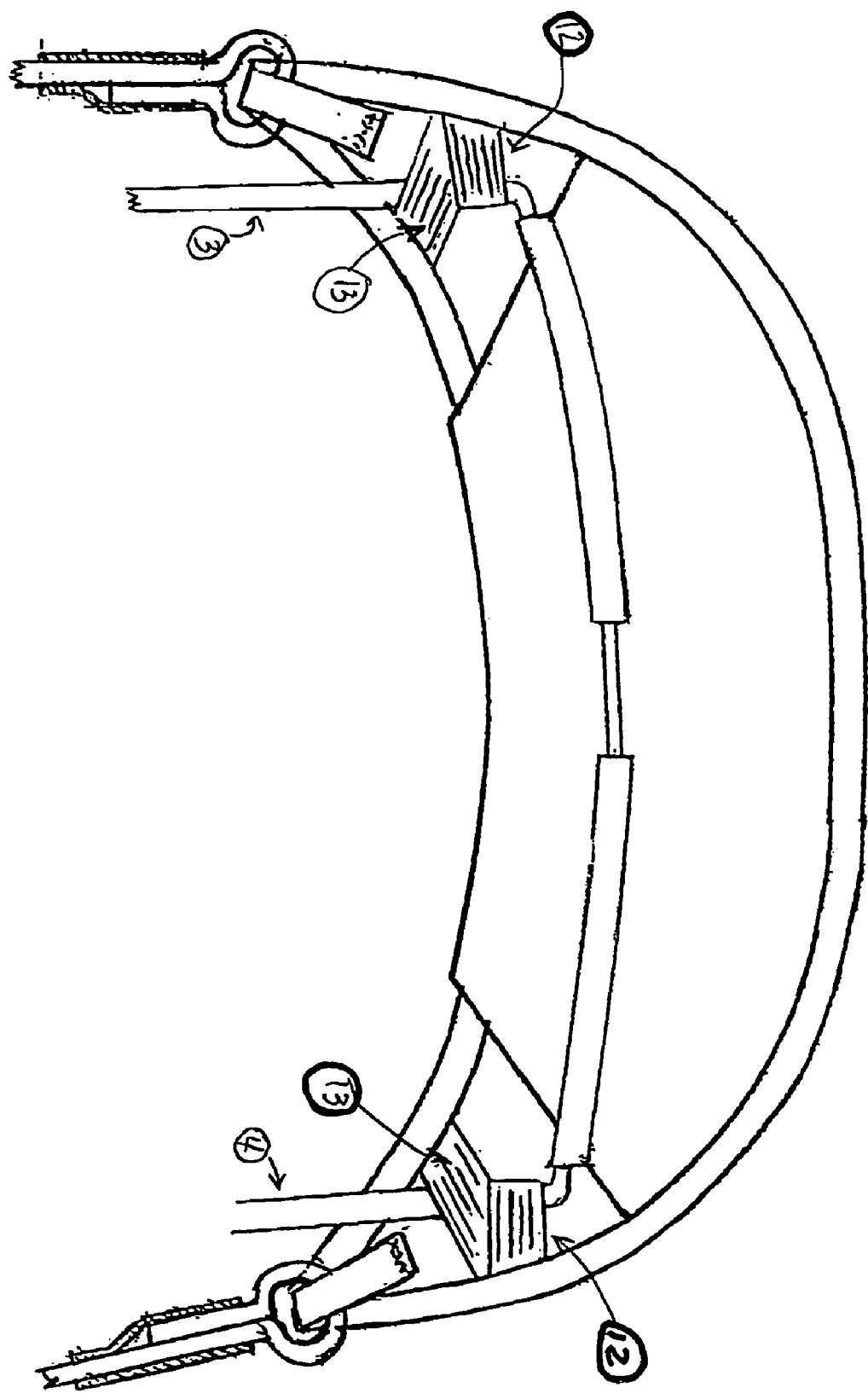
FIG. 4 is a bottom view of the visor and case showing the attachment bands on the exposed bottom of the top ply with an eyeglass limb inserted into the attachment bands.

As shown in FIG. 3 two sets of short lengths of elastic band material (12) and (13) are sewn into the bottom of the top ply (5) near the corners in the general area where the corners are removed from the bottom ply (6). The first band material (12) is folded double and attached to the convex edge (7) so as to form a loop that protrudes downwardly from the bottom of the top ply (5). The second band material (13) is attached diagonally across the corner laying flat against the bottom of the top ply (5). The size of the loops is carefully chosen so as to be suitable so that the limbs (3) and (4) of a conventional pair of eyeglasses may fit through both the looped band (12) and the flat band (13) as required by the limb (3,4) size and shown in FIG. 4. Preferably, the band material will be required to stretch slightly to receive the limbs (3) and (4), so that the loops (12) and flat bands (13) function to support the visor (1) snuggly to the eyeglasses and in a stable position above the lenses of the eyeglasses at the user's forehead. The combination of the bands used together allow the eyeglasses to fit snugly to the glasses and accommodate the widest variety of eyeglass limbs.

Figure 5:
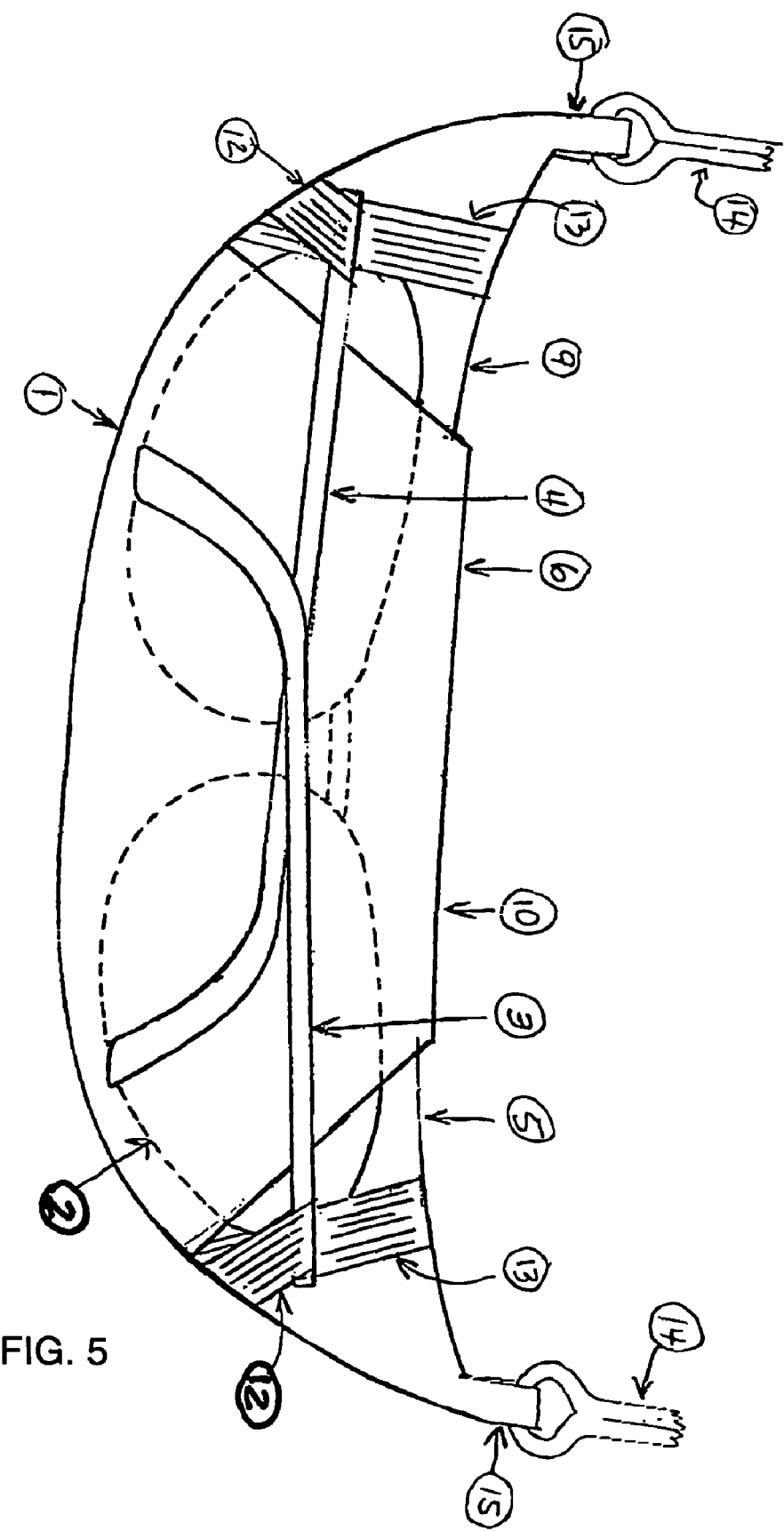
FIG. 5 is a perspective illustration of the eyeglasses visor and case, showing how a pair of eyeglasses is stored within the pocket without being detached from the visor.

If the eyeglasses are removed from the face of the wearer and the limbs are folded across the lenses with visor case still attached to the eyeglasses as illustrated in FIG. 5, the missing corners of the bottom ply allows the bottom ply to be widely opened for insertion of the folded eyeglasses into the pocket without removal of the limbs (3, 4) from the bands (12, 13). As illustrated in the figure, the top and bottom plies of material (5) and (6) can be separated by opening the visor case at the non-attached edges (9, 10), which exposes the pocket. The pair of eyeglasses (2) can be inserted in the pocket formed between the plies of material, with the limbs (3, 4) of the eyeglasses folded across the lenses. The limbs may be inserted to either the outside or inside of the pocket as users prefer. Once the eyeglasses have been inserted inside the visor case (1), the bottom ply (6) of the visor case (1) can be folded up, over and attached to the top ply (5) to hold the eyeglasses (2) in by the fastening means (11). Of course, while the visor case is not occupied by the eyeglasses (2) other objects such as money, a key, or identification document can be stored in the pocket of the visor (1).

A lanyard (14) can be added, as shown in FIG. 5, as either a permanent attachment such as a heat-shrink attached lanyard cord or a removable attachment using appropriate fasteners such that the visor case (1) can hang around the user's neck and rest against the user's chest when not being worn, either in a visor mode (eyeglasses (2) and visor (1) deployed together) or case mode (eyeglasses (2) attached and inserted into visor case (1)). The removable lanyard attachment may function such that the lanyard (14) can be removed from lanyard attachment connectors (15) on the visor (1) and attached directly to the eye glass limbs (3, 4) while the unique attachment bands continue to firmly hold the visor (1) and eyeglasses together. The lanyard attachment connectors (15), when a lanyard is not attached, can be used to secure the visor (1) to other objects such as belts, belt loops, backpacks and purses.

Although this invention has been described in the form of a preferred embodiment, many modifications, additions, and deletions, may be made thereto without departure from the spirit and scope of the invention, a set forth in the following claims.

What is claimed is:

1. An eyeglass case and visor to be mounted to the eyeglass limbs of a pair of eyeglasses or the like and worn in front of the forehead and above the eyeglasses to shade the eyes comprising:
   a) an upper ply of approximately crescent-shaped material having a concave edge for placement adjacent to the forehead and a convex edge for extending away from the forehead;
   b) said concave edge and said convex edge meeting at corners and having eyeglass limbs attachment means fixed to the bottom side of said upper ply of material near to said corners;
   c) a lower ply of approximately triangular-shaped material wherein one edge of said lower ply has a convex shape resulting in a convex edge of said lower ply matching said convex edge of said upper ply but shorter in length such that said eyeglass limbs attachment means fixed to said corners of said upper ply are not covered by said lower ply when said upper ply and said lower ply are aligned in an overlying relationship;
   d) said lower ply and said upper ply being aligned in an overlying relationship and being attached to each other along their convex edges to form a pocket therebetween;
   e) said pocket formed by said upper ply and said lower ply being of a size large enough to substantially contain the eyeglasses when the eyeglass limbs are folded without detaching the eyeglasses from said limb attachment means; and,
   f) a releasable ply connection means attached to said upper ply and said lower ply for releasably closing said pocket.

2. The eyeglass case and visor of claim 1 wherein said releasable ply connection means comprises a first connector member attached to the upper side of said lower ply of material at the angle opposite said convex edge of said lower ply material and a second connector member attached to the upper side of said upper ply of material such that when said bottom ply of material is folded up and around said concave edge of said upper ply of material said first connector member and said second connector member align and detachably connect whereby eyeglasses can be placed in said pocket and the releasable ply connection means can close said pocket about the eyeglasses.

3. The eyeglass case and visor of claim 1 wherein said limb attachment means each comprise one or more bands of flexible material through which the limbs of eyeglasses are received.

4. The eyeglass case and visor of claim 1 and wherein said limb attachments means each comprises a first band of flexible material formed in a loop and with the ends of the first band sewn together and to said upper ply, and a second band of elastic material laid flat across the upper ply of material and attached at said second band ends to said upper ply, whereby when the limbs of a pair of eyeglasses are received in either or both of said first or second band of flexible material the attachment means tend to support the eyeglass case and visor in front of and above the eyeglasses and the attachment means work to snug the visor to the eyeglasses such that the use of either or both of said first or second band of flexible material depends on the specific thickness attribute of said eyeglass limbs and use of these attachment means accommodates a wide variety of eyeglass limbs.

5. An eyeglass case and visor to be mounted to the eyeglass limbs of a pair of eyeglasses or the like and worn in front of the forehead and above the eyeglasses to shade the eyes comprising:
   a) an upper ply of approximately crescent-shaped material having a concave edge for placement adjacent to the forehead and a convex edge for extending away from the forehead;
   b) said concave edge and said convex edge meeting at corners and having eyeglass limbs attachment means fixed to the bottom side of said upper ply of material near to said corners;
   c) a lower ply of approximately triangular-shaped material wherein one edge of said lower ply has a convex shape resulting in a convex edge of said lower ply matching said convex edge of said upper ply but shorter in length such that said eyeglass limbs attachment means fixed to said corners of said upper ply are not covered by said lower ply when said upper ply and said lower ply are aligned in an overlying relationship;
   d) said lower ply and said upper ply being aligned in an overlying relationship and being attached to each other along their convex edges to form a pocket therebetween;
   e) said pocket formed by said upper ply and said lower ply being of a size large enough to substantially contain the eyeglasses when the eyeglass limbs are folded without detaching the eyeglasses from said limb attachment means;
   f) a releasable ply connection means attached to said upper ply and said lower ply for releasably closing said pocket; and,
   g) a lanyard attached at the corners of said upper ply of material.

6. The eyeglass case and visor of claim 5 wherein said releasable ply connection means comprises a first connector member attached to the upper side of said lower ply of material at an angle opposite said convex edge of said lower ply material and a second connector member attached to the upper side of said upper ply of material such that when said bottom ply of material is folded up and around said concave edge of said upper ply of material said first connector member and said second connector member align and detachably connect whereby eyeglasses can be placed in said pocket and the releasable ply connection means can close said pocket about the eyeglasses.

7. The eyeglass case and visor of claim 5 and wherein said limb attachment means each comprise one or more bands of flexible material through which the limbs of eyeglasses are received.

8. The eyeglass case and visor of claim 5 wherein said limb attachments means each comprises a first band of flexible material formed in a loop and with the ends of the first band sewn together and to said upper ply, and a second band of flexible material laid flat across the upper ply of material and attached at said second band ends to said upper ply, whereby when the limbs of a pair of eyeglasses are received in either or both of said first or second band of flexible material the attachment means tend to support the visor in front of the eyeglasses and the attachment means work to snug the visor to the eyeglasses such that the use of either or both of said first or second band of flexible material depends on the specific thickness attribute of said eyeglass limbs and use of these attachment means accommodates a wide variety of eyeglass limbs.

9. The eyeglass case and visor of claim 5 wherein said visor further comprises a permanently attached lanyard connector at the corners of said upper ply of material to which said lanyard can be releasably attached and said lanyard connector allows the eyeglass case and visor to be releasably connected to said lanyard or to a belt, belt loop, backpack, purse or other similar article of the user.

10. An eyeglass case and visor to be mounted to the eyeglass limbs of a pair of eyeglasses or the like and worn in front of the forehead and above the eyeglasses to shade the eyes comprising:
   a) an upper ply of approximately crescent-shaped material having a concave edge for placement adjacent to the forehead and a convex edge for extending away from the forehead;
   b) said concave edge and said convex edge meeting at corners and having eyeglass limbs attachment means fixed to the bottom side of said upper ply of material near to said corners wherein said limb attachments means each comprises a first band of flexible material formed in a loop and with the ends of the first band sewn together and to said upper ply, and a second band of flexible material laid flat across the upper ply of material and attached at said second band ends to said upper ply, whereby when the limbs of a pair of eyeglasses are received in either or both of said first or second band of flexible material the attachment means tend to support the visor in front of the eyeglasses and the attachment means work to snug the visor to the eyeglasses such that the use of either or both of said first or second band of flexible material depends on the specific thickness attribute of said eyeglass limbs and use of these attachment means accommodates a wide variety of eyeglass limbs;
   c) a lower ply of approximately triangular-shaped material wherein one edge of said lower ply has a convex shape resulting in a convex edge of said lower ply matching said convex edge of said upper ply but shorter in length such that said eyeglass limbs attachment means fixed to said corners of said upper ply are not covered by said lower ply when said upper ply and said lower ply are aligned in an overlying relationship;
   d) said lower ply and said upper ply being aligned in an overlying relationship and being attached to each other along their convex edges to form a pocket therebetween;
   e) said pocket formed by said upper ply and said lower ply being of a size large enough to substantially contain the eyeglasses when the eyeglass limbs are folded without detaching the eyeglasses from said limb attachment means;
   f) a releasable ply connection means attached to said upper ply and said lower ply for releasably closing said pocket wherein said releasable ply connection means comprises a first connector member attached to the upper side of said lower ply of material at said angle opposite said convex edge of said lower ply material and a second connector member attached to the upper side of said upper ply of material such that when said bottom ply of material is folded up and around said concave edge of said upper ply of material said first connector member and said second connector member align and detachably connect whereby eyeglasses can be placed in said pocket and the releasable ply connection means can close said pocket about the eyeglasses; and,
   g) a lanyard connection means attached at the corners of said upper ply of material wherein said lanyard connection means comprises a permanently attached lanyard connector wherein said lanyard connector allows the eyeglass case and visor to be releasably connected to a lanyard, belt, belt loop, backpack, purse or other similar article of the user.

* * * * *